United States Patent [19]

Cunningham

[11] 4,200,119
[45] Apr. 29, 1980

[54] ADJUSTABLE FLUID FLOW RESTRICTOR

[76] Inventor: Patrick J. Cunningham, 600 N. Ladera Vista, Fullerton, Calif. 92631

[21] Appl. No.: 903,955

[22] Filed: May 8, 1978

[51] Int. Cl.$^2$ ............................................. F16K 1/52
[52] U.S. Cl. .................................. 137/605; 251/117; 138/45; 138/40
[58] Field of Search ................. 251/117, 122; 138/45, 138/46, 43, 40; 137/513.3, 605

[56] References Cited

U.S. PATENT DOCUMENTS

| 136,746 | 3/1873 | McMahon | 251/117 X |
|---|---|---|---|
| 521,440 | 6/1894 | Robinson | 137/513.3 X |
| 2,265,888 | 12/1941 | Beck | 251/122 X |
| 3,139,114 | 6/1964 | Benzel | 138/45 |
| 3,675,891 | 7/1972 | Reynolds et al. | 251/117 |

*Primary Examiner*—Arnold Rosenthal
*Attorney, Agent, or Firm*—Raymond L. Madsen

[57] ABSTRACT

There is disclosed an adjustable fluid flow restrictor for controlling the rate of fluid flow into a conduit, the restrictor having a body which seals the central opening of a fluid chamber and through which body there is a central opening having a cylinder section and a truncated cone section the cylinder section having a set-screw engaged therein, the threads thereof forming spiral grooves through which fluid maybe conducted at a rate controlled by positioning the end of the set-screw adjacent the walls of the truncated cone section to obstruct and adjustably close the openings into the spiral grooves thereby restricting the rate of fluid flow. An alternate form of the restrictor employs a ball-valve between the set-screw and the truncated cone section, the space between the ball-valve and the walls of the truncated cone section being adjusted by the set-screw to restrict the flow of fluid. Longitudinal ridges maybe added to the walls of the truncated cone section to prevent complete obstruction of the truncated cone section by the ball-valve for more accurate control of slow fluid rates. The restrictor body itself may be used as a by-pass valve by being moveably located in the fluid chamber and biased against a valve seat formed around the central opening of the fluid chamber. A plunger is moveably mounted through the walls of the fluid chamber to contact and push the restrictor body away from the valve seat and allow fluid to pass around the restrictor and by-pass the internal flow of fluid through the restrictor.

10 Claims, 4 Drawing Figures

ADJUSTABLE FLUID FLOW RESTRICTOR

The present invention relates to fluid metering devices in more particularly to adjustable fluid flow resistors and restrictors for the introduction of minute amounts of fluid over controlled periods of time for medical and chemical purposes. In the field of medicine, it has been the general practice to employ continuous flushing systems to continuously flush the catheter of a cannulated artery or vein used for pressure monitoring to prevent oclusion of the intervascular catheter and blood clotting and to maintain the catheter clear of obstruction for long periods of time required to record arterial pulse wave forms to obtain such parameters as stroke volume, heart rate, cardiac output, duration of systole, and systolic, diastolic and mean blood pressure. Such continuous flushing systems have utilized flow rates adjustable by stopcocks. Although such control elements have been served the purpose, they have not proved entirely satisfactory under all conditions of service for the reason that considerable difficulty has been experienced in minute leaks and the inability to maintain high quality stopcock integrity. Marine-bore capulary tubes have been used as flow resistors in continuous flushing systems by applying the flushing solution under pressure through the timing capulary. One such marine-bore flushing apparatus is described in U.S. Pat. No. 3,675,891 entitled Continuous Catheter Flushing Apparatus granted to Gordon S. Reynolds et. al. The apparatus includes a resilient valve for controlling a by-pass around a marine-bore flow resistor. Although this apparatus has served the purpose it is not proved entirely satisfactory under all conditions of service for the reason that difficulty has been experienced in obtaining desired fluid flow or drip rates through the device.

For the percutaneous introduction of catheters and pacing leads into patients, a catheter sheath introducer system is utilized. The sheath assembly must be flushed with a solution such as a heparinized saline solution to remove any air. Thereafter, a heparin drip fluid flow is introduced into a side port extension using a pressurized system. Those concerned with the development of catheter sheath introducer systems have long recognized the need for an adjustable fluid flow restrictor which can maintain the required fluid drip rate. The present invention fulfills this need.

The general purpose of this invention is to provide a fluid flow restrictor and continuous catheter flushing device which embraces all the advantages of similarly employed fluid restrictors and continuous flushing systems of possess none of the aforedescribed disadvantages. To obtain this, the present invention contemplates a unique restrictor plug and setscrew fluid restrictor adjustment whereby undetermined, unstable and inaccurate fluid flow rates are avoided.

An object of the present invention is the provision of a preset accurate fluid flow rate through a fluid flow restrictor.

Another object is to provide a fluid flow restrictor which is adjustable and disposable.

A further object of the invention is the provision of a valve controlling a by-pass around an adjustable fluid flow restrictor which is leak proof, fail safe, and quick acting.

Still another object is to provide a fluid flow restrictor which forms a valve to by-pass fluid around the fluid restrictor.

Yet another object of the present invention is the provision of preadjusted accurate rates of drip fluid flow into a catheter.

Other objects and many of the attendant advantages of this invention will be readily appreciated as the same becomes understood by reference to the following detailed description when considered in connection with the accompanying drawings in which like reference numerals designate like parts throughout the figures thereof and wherein.

Figure 1:
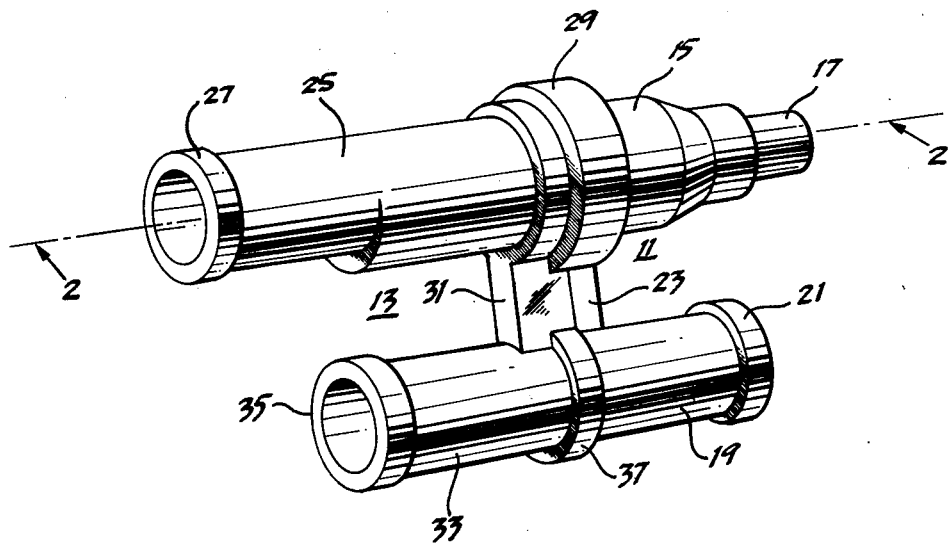
FIG. 1 illustrates a diagrammatic view, partly in side elevation of a preferred embodiment of the invention.

Referring now to the drawings, wherein like reference character designate like or corresponding parts throughout the several views, there is shown in FIG. 1 (which illustrates a preferred embodiment) a fluid flow restrictor and conduit or catheter flushing device having a cap member 11 and a body member 13, the cap member 11 having a cylindrical housing 15 therein containing a button, shaft, or plunger element 17 therein. Cap 11 further has a conduit section 19 with a collar or flange 21 around one end thereof. Conduit section 19 is joined to cylindrical housing 15 by a bridge member 23.

Body member 13 has a control housing or chamber 25 with a connecting collar or flange 27 formed at one end thereof and a collar or receptacle 29 at the other end thereof which mates with and engages the base of cylindrical housing 15. A bridge member 31 mates with and engages bridge member 23 and connects control chamber 25 with a conduit section 33. Conduit section 33 has a collar or flange connector 35 at one end thereof and a receptacle or collar 37 at the other end thereof which mates with and engages the other end of conduit section 19.

Cap member 11 and body member 13 maybe fabricated as two integral parts molded of rigid plastic material, preferable transparent. Cap 11 and body member 13 maybe secured together cementitiously, by a solvent or other suitable fushing or welding process.

Connecting collars or flanges 21, 27 and 35 may be formed into any desired shape or structure to mate with any desired interconnecting tube, conduit, cannula or catheter and the like, as required or desired.

Figure 2:
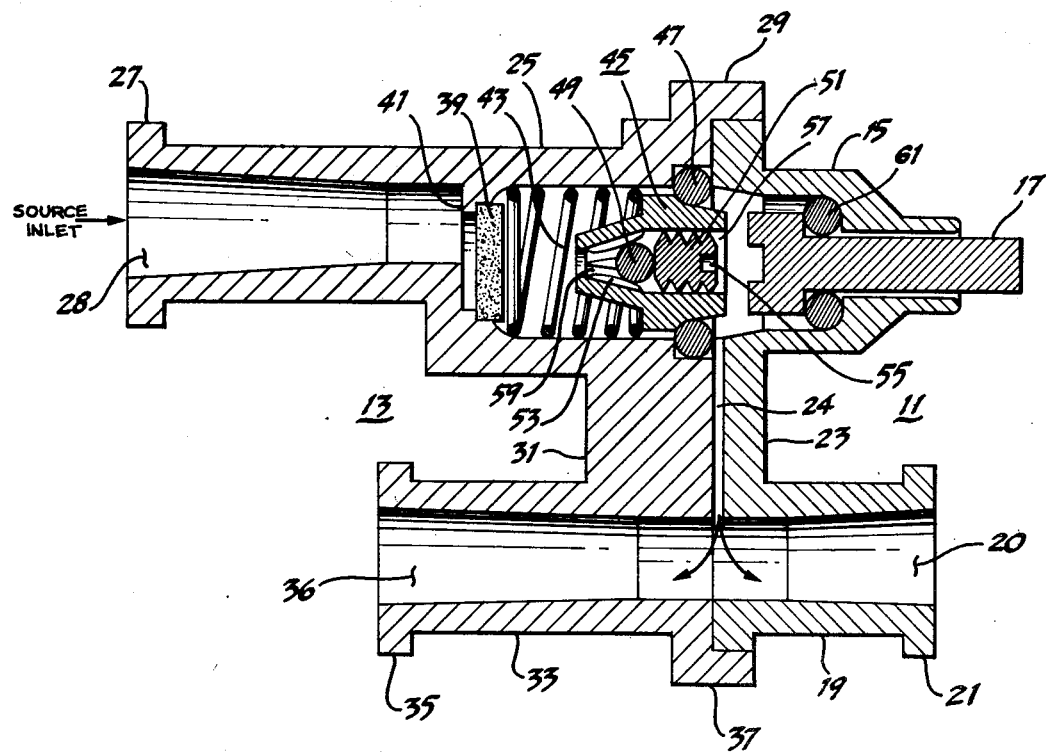
FIG. 2 shows a section of the device taken on the line 2—2 of FIG. 1 looking in the direction of the arrows.

Turning now to FIG. 2 which is the cross-section of the device illustrated in FIG. 1, control chamber 25 has an opening or port 28 through collar 27 into the interior thereof where a filter 39 is fixedly held in place by a spring 43 which biases a restrictor plug 45 against an "0" ring 47 held in place within collar 29 by cap 11.

Restrictor or plug 45 has a central opening therethrough which has a cylinder section 57 with a threaded set-screw 51 frictionally engaged therein, set-screw 51 having a hexagonal opening 55 therein adapted to receive a wrench for adjusting the position of set-screw 51 within cylinder section 57.

Cylinder section 57 in turn connects to the base of a truncated cone section 59. Truncated cone section 59 has longitudinal ribs 53 therealong which contact and guide a ball-valve 49 which in turn is in contact with one end of set-screw 51.

It should be noted that ball-valve 49 and grooves 53 maybe eliminated from restrictor plug 45 and that setscrew 51 maybe used by itself to adjust the flow rate of fluid through restrictor plug 45 by advancing the set-screw into engagement with the walls of truncated cone section 59.

Button or plunger or shaft 17 extends through cylindrical housing 15 and is held in a fluid tight seal therein by an "O" ring seal 61, which allows plunger 17 to be depressed into cylindrical housing 15 and not allow fluid to leak out around plunger 17.

Filter 39 may be a micron filter which prevents clogging of the fluid flow restrictor plug and eliminates bacteria that maybe in the infusion solution. Coil spring 43 may be of an inert metal such as terngsten, solatinium and other like metals suitable for use with the fluid solution being dispensed. "O" rings 47 and 61 maybe of a flexible and compressable material such as rubber and neoprene and the like.

Input port 28 of control chamber 25 connects through filter 39 and restrictor plug 51 to a fluid slot 24 located between bridge members 23 and 31. Fluid slot 24 connects with the interior of conduit sections 19 and 33 and to port 20 in conduit section 19 and a port 36 in conduit section 33. Conduit sections 19 and 33 maybe inturn connected to a catheter and associated tubing which are desired to be flushed by a fluid source connected to port 28 of control chamber 25.

Figure 3:
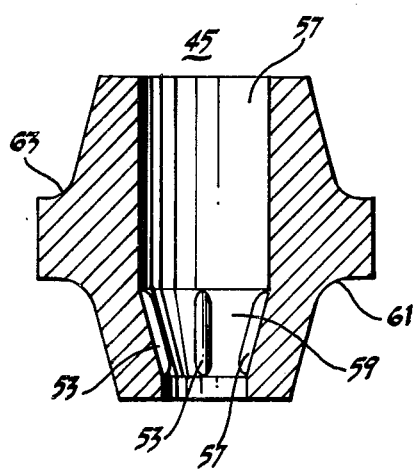
FIG. 3 is a section of the restrictor illustrated in FIG. 2.

Restrictor plug 45 of FIG. 2 is shown in enlarged detail in FIG. 3. The central opening through plug 45 comprises cylinder section 57 and truncated cone section 59 with truncated cone section 59 containing longitudinal ridges 53 therein. Restrictor plug 45 is generally cylindrical in shape with a large diameter central section having a circumferential groove 61 on one side thereof and a circumferential groove 63 on the other side thereof. Groove 61 is substantially around the truncated cone section and groove 63 is located around the cylinder section portion of plug 45. Groove 61 is constructed and arranged to receive one end of the circular coils of spring 43 and groove 63 is constructed and arranged to mate with and engage the surface of "O" ring 47.

Figure 4:
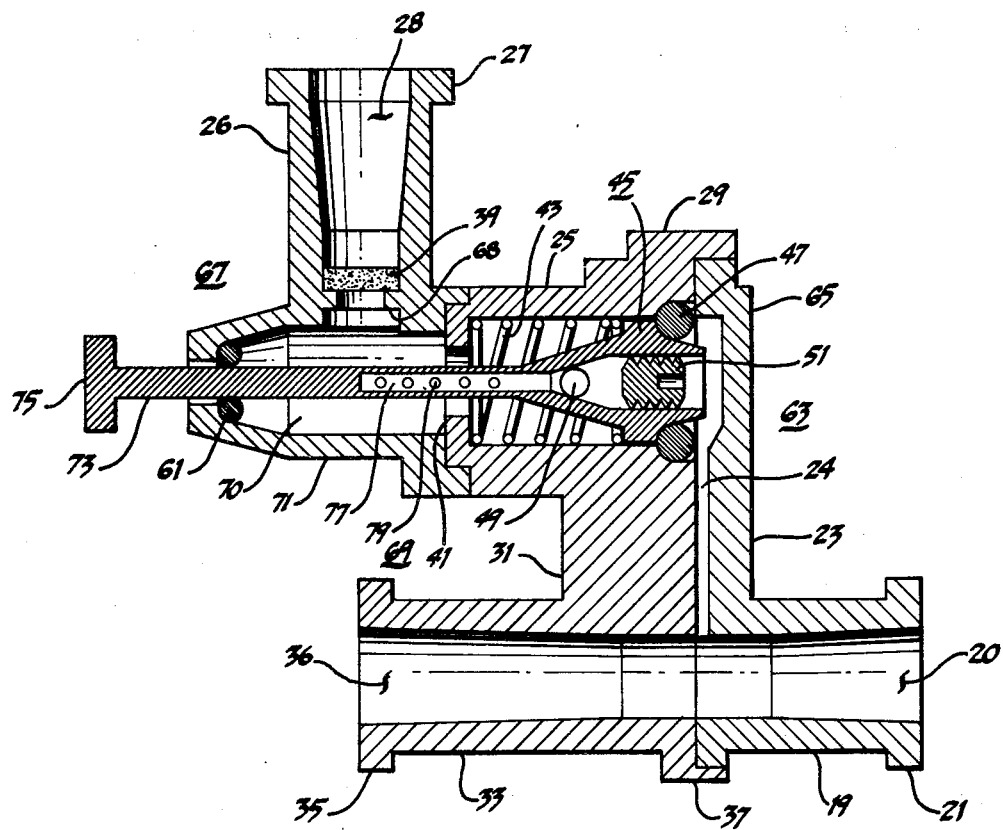
FIG. 4 illustrates a section of another version of the embodiment of FIG. 2.

In FIG. 4 a cap member 63 and a body member 69, the cap member 63 having a cover section 65 connected to conduit section 19 by bridge member 23. Body member 69 contains central chamber 25 and further has a housing member 67 connected thereto housing member 67 having a cylinder section 71 with a central channel 70 therein which mates with the interior of control chamber 25. Central channel 70 is connected to conduit section 26 which contains filter 39 held in place by a collar 68. Housing member 67 has an opening therethrough through which a shaft 73 passes and is moveably sealed therein by "O" ring 61. Shaft 73 has a head 75 thereon which is shaped to be easily grasped by the fingers of a person operating the device. Shaft 73 passes through central channel 70 and is connected to restrictor plug 45. The end of shaft 73 which is connected to plug 45 has a hollow interior 77 which has holes 79 therethrough through which fluid may flow from control chamber 25 into the interior of plug 45.

Operation of the invention can best be described in turning to FIG. 2. A source of fluid or liquid to be introduce or metered into conduit section 19 and 33 is connected to port 28 of control chamber 25. The fluid then passes through filter 39 and into the central opening through restrictor plug 45. Fluid then flows past ball-valve 49 which is pressed against ridges 53 by set-screw 51. Set-screw 51 maybe adjusted to allow ball valve 49 to be more or less loosely positioned against ribs 53 to allow a greater or less opening for fluid to pass through truncated cone section 59. Ball-valve 49 maybe forced tightly against ribs 53 or ridges 53 to cause the ridges to compress and therefore produce a very small opening between ball-valve 49 and truncated cone section 59 to accurately control low fluid flow rates. It should also be noted that the ridges 53 maybe eliminated so that ball-valve 49 could, at on extreme adjustment of the set-screw close completely any opening between ball-valve 49 and truncated cone section 59.

Depending upon the adjustment of set-screw 51 in respect to ball-valve 49, fluid flows pass ball valve 49 and into the threaded grooves of set-screw 51. The threads of set-screw 51 frictionally engage the surface of cylinder section 57 and form grooves between the walls of cylinder section 57 and the threads of set-screw 51 through which fluid may easily flow. The cross-section of these grooves is sufficiently large enough so as not to impede or to restrict the fluid flow in the range of fluid flow rates over which adjustment is desired. The set-screw of restrictor plug 45 is generally preset during manufacturing assembly to obtain a desired flow rate.

Fluid leaves the threads of set-screw 51 and enters into passage 24 where it exits in the direction of the arrows into conduit sections 19 and 33.

In normal operation, spring 43 biases restrictor plug 45 against "O" ring 47 to close off any fluid flow through control chamber 25 except by way of central opening through restrictor plug 45. However, there are times when it is desired to obtain a very rapid fluid flow without control restriction. This is obtained by depressing plunger or button 17 so as to engage restrictor plug 45 to force groove 63 out of engagement with "O" ring 47 and allow fluid to flow around restrictor plug 45 and by-pass the restricted flow through the center of restrictor plug 45. When plunger or button 17 is released, spring 43 biases restrictor plug 45 back into engagement with "O" ring 47 to seal the fluid by-pass and prevent the escape of fluid pass restrictor plug 45 and further returns plunger or button 17 back to its original position.

It should be pointed out that restrictor plug 45 maybe permanently mounted in a conduit where groove 63 would be sealed to a mounting surface within the conduit to keep restrictor plug 45 ridgedly positioned therein. This assembly creates a preadjustable fluid restrictor for applications in which the by-pass feature is not required.

When grooves 53 and ball valve 49 are eliminated from restrictor plug 45, set-screw 51 is turned until one end of it is adjacent the surface of truncated cone section 59. By turning set-screw 51 further into truncated cone section 59 the openings into the grooves between the threads are closed off and restrict the flow of fluid through the grooves. Therefore an adjustable restricted flow rate maybe obtained by use of the set-screw alone without the ball-valve assembly.

The by-pass feature shown in FIG. 4 operates by pulling head 75 of shaft 73 outwardly against bias spring 43 to lift plug 45 off "O" ring seat 47 and allow a fast fluid flow around plug 45 to by-pass 45. During normal slow flow rates, plug 45 is seated against "O" ring 47 and seals the opening therethrough. In this sealed position fluid enters through holes 79 of shaft 73 into the shaft interior 77 and therefrom into the restricted interiors volume of plug 45.

It is important to note that with the by-pass mechanical arrangement shown in FIG. 4, the problems of leaking seals around the shaft of the button or plunger 17 of FIG. 2 altering or affecting fluid flow rates are avoided as well as possible contamination through the seal at the lower fluid pressure, the seal in FIG. 4 being on the high fluid pressure side of the flow restrictor.

It now should be apparent that the present invention provides a mechanical fluid restrictor arrangement which maybe employed in conjunction with continuous flushing systems for providing a present restricted fluid flow rate which is accurate and reliable and easily reproduced.

Although particular components, etc. have been discussed in connection with a specific embodiment of a fluid flow restrictor constructed in accordance with the teachings of the present invention, others maybe utilized. Furthermore, it will be understood that although exemplary embodiment of the present invention has been disclosed and discussed, other applications and similar arrangements are possible and that the embodiment disclosed maybe subjected to various changes, modifications, and substitutions without necessarily departing from the spirit of the invention.

What is claimed is:

1. An adjustable restrictor for controlling the rate of fluid flow into a conduit, comprising:
    a body member having a section of conduit defining a continuous unrestricted fluid path within the walls and ends thereof, said body member having a control chamber adapted to receive a fluid flow restrictor said body member having a fluid passage connected between said control chamber and said section of conduit, said body member having an inlet port connected to said control chamber and adapted to be connected to a source of fluid to be controllably dispensed into said section of conduit; and
    a fluid flow restrictor positioned in said control chamber between said inlet port and said fluid passage for restricting the flow of fluid between said inlet port and said fluid passage, said fluid flow restrictor having a central opening therethrough, said central opening having a cylinder section and a truncated cone section, said cylinder section being connected to the base of said truncated cone section, said cylinder section having a threaded set-screw engaged therein whereby fluid may traverse the spiral grooves between said threads of said set-screw and the walls of said cylinder section, said set-screw being rotated into said cylinder section to encounter the walls of said truncated cone section thereby obstructing the openings into said spiral grooves between said threads and said walls of said cylinder section and restricting the rate of fluid flow through said spiral grooves.

2. The adjustable restrictor described in claim 1 further including a ball-valve moveable located between said set-screw and the walls of said truncated cone section, said ball-valve being adjustably positioned adjacent said walls of said truncated cone section by rotating said set-screw thereby controlling the rate of fluid flow through the threads of said set-screw.

3. The adjustable restrictor described in claim 2 further including a plurality of longitudinal ridges along the walls of said truncated cone section for engaging said ball-valve, the grooves between said ridges forming an adjustable opening past said ball-valve which opening is controlled by said set-screw forcing said ball-valve into compressive engagement with said ridges.

4. The adjustable restrictor described in claim 1 wherein said fluid flow restrictor is moveably positioned in said control chamber and further including:
    a valve opening and a valve seat therearound located in said control chamber and through which valve opening fluid may pass from said inlet port to said fluid passage when said valve opening is unobstructed;
    bias means connected between said control chamber and said fluid flow restrictor for biasing said fluid flow restrictor in said valve opening and against said valve seat to close said valve opening thereby preventing fluid flow through said valve opening and permitting restricted flow through said central opening of said fluid flow restrictor; and
    button means moveably mounted through the walls of said control chamber and forming a fluid tight seal therein, said button means contacting said fluid flow restrictor and moving said fluid flow restrictor against the bias means and away from said valve seat to open said valve opening when said button is depressed thereby allowing fluid to flow around and by-pass said fluid flow restrictor.

5. The adjustable restrictor described in claim 1 wherein said fluid flow restrictor is moveably positioned in said control chamber and further including:
    a valve opening and a valve seat therearound located in said control chamber and through which valve opening fluid may pass from said inlet port to said fluid passage when said valve opening is unobstructed;
    bias means connected between said control chamber and said fluid flow restrictor for biasing said fluid flow restrictor in said valve opening and against said valve seat to close said valve opening thereby preventing fluid flow through said valve opening and permitting restricted flow through said central opening of said fluid flow restrictor; and
    shaft means moveably mounted through the walls of said control chamber and forming a fluid tight seal therein, said shaft means connected to said fluid flow restrictor and moving said fluid flow restrictor against and bias means and away from said valve seat to open said valve opening when said shaft means is pulled thereby allowing fluid to flow around and by-pass said fluid flow restrictor, said shaft means having holes through the walls thereof communicating with a hollow interior, said hollow interior being connected to said central opening of said fluid flow restrictor.

6. A fluid flow restrictor for location in the central opening of a fluid conduit, comprising:
    a plug for sealing the central opening of a fluid conduit, said plug having a central opening therethrough, said central opening having a cylinder section and a truncated cone section, said cylinder section having unthreaded walls and merging with the base of said truncated cone section; and
    a set-screw rotatably engaged in said cylinder section and said plug and forming a fluid path along the spiral grooves between the threads of said set-screw and the unthreaded walls of said cylinder section, said set-screw being rotated into position adjacent the walls of said truncated cone section thereby adjustably closing the openings into said spiral grooves to restrict the rate of fluid flow therethrough.

7. The fluid flow restrictor described in claim 5 further including a ball-valve moveably located between said set-screw and the walls of said truncated cone section, said ball valve being adjustably positioned adjacent said walls of said truncated cone section by rotating said set-screw thereby controlling the rate of fluid flow through the threads of said set-screw.

8. The fluid flow restrictor described in claim 6 further including:
   a ball valve moveably located within said truncated cone section; and
   a plurality of longitudinal ridges along the walls of said truncated cone section for engaging said ball valve and forming an adjustable opening past said ball valve which is controlled by said set-screw forcing said ball valve into compressive engagement with said ridges.

9. A continuous flow control apparatus, comprising:
   a body member having passages therein defining a continuously open inlet-outlet path through the body member;
   a flow restrictor in the form of a plug having a central opening therethrough containing a cylinder section connected to a cone section and having a set-screw engaged in said cylinder section and adjustably rotated into said truncated cone section to control the openings into the threaded grooves of said set-screw to control the rate of fluid flow through the central opening of said flow restrictor;
   said body member having other passages therein defining a by-pass around the part of said path containing said flow restrictor which by-pass is of size to permit a fast flow of liquid, said by-pass being shaped to provided a valve seat; and
   and a valve means having a shaft associated therewith and projecting out of said body, said valve means being positioned in said by-pass and so mounted as to forceably press against said valve seat and automatically close when said shaft is released.

10. The continuous flow apparatus described in claim 9 wherein said shaft is integrally attached to said valve means and said valve means is lifted from said valve seat by pulling said shaft outwardly from said body.

* * * * *